United States Patent [19]
Silver

[11] Patent Number: 6,078,681
[45] Date of Patent: *Jun. 20, 2000

[54] ANALYTICAL IMAGING SYSTEM AND PROCESS

[75] Inventor: Robert B. Silver, Woods Hole, Mass.

[73] Assignee: Marine Biological Laboratory, Wood Hole, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/618,246

[22] Filed: Mar. 18, 1996

[51] Int. Cl.$^7$ .............................. G06K 9/00; G01N 21/64
[52] U.S. Cl. .......................... 382/133; 382/284; 356/435; 250/461.2
[58] Field of Search ................................ 356/417, 426, 356/435; 382/284, 133, 128; 250/461.2; 348/46, 47, 79, 218, 135

[56] References Cited

U.S. PATENT DOCUMENTS

| | | | |
|---|---|---|---|
| 4,744,667 | 5/1988 | Fay et al. | 356/417 |
| 4,755,874 | 7/1988 | Esrig et al. | 358/106 |
| 5,332,905 | 7/1994 | Brooker et al. | 250/458 |
| 5,369,496 | 11/1994 | Alfano et al. | 356/446 |
| 5,488,674 | 1/1996 | Burt et al. | 382/284 |
| 5,528,046 | 6/1996 | Ishikawa | 250/461.2 |

FOREIGN PATENT DOCUMENTS 0 270 251 A2  6/1988  European Pat. Off. .......... G01T 1/29
0 404 568 A2  12/1990  European Pat. Off. ........ G06F 15/72

Primary Examiner—Matthew C. Bella
Attorney, Agent, or Firm—Hale and Dorr LLP

[57] ABSTRACT

An image system captures and records optical and photon images of an activity, such as cellular phenomena. The images are simultaneously recorded on videotape and displayed. Image data is processed and stored for later analysis and for comparison to new data.

33 Claims, 5 Drawing Sheets

ANALYTICAL IMAGING SYSTEM AND PROCESS

FIELD OF THE INVENTION

This invention relates to a system and process for imaging and analyzing a specimen during an activity.

BACKGROUND OF THE INVENTION

Living cells and tissues perform and coordinate hundreds to thousands of individual processes, and control the location, orientation, and state of assembly of many structural components in the course of normal life. These processes are usually performed by, and structures are comprised of, specialized groups and classes of molecules. Biologists have used light microscopes to study these processes, both in living cells and in cells that have been preserved at particular points in the cells' lives. Study of these processes or structures involves the detection of molecules or reactions as signals that are often processed and analyzed to help the biologist learn and understand the particular process or structure. Such detection typically relies on a characteristic interaction of light with the molecules responsible for the process or structure that is subject to study. Because components such as molecules are dynamic in living cells and act in concert with, and rely upon, interactions among similar and dissimilar components, it is desirable to study the relationship of a component with one or more other components in a cell.

SUMMARY OF THE INVENTION

The present invention includes an image processing system and process for imaging a specimen during an activity, such as biological, physical, or chemical activity, to analyze the specimen during the activity. The system receives and records different spectral images, preferably a visible image and a low intensity photonic image, and synchronously records them, preferably in real time on an image-recording media, such as a video cassette recorder (VCR) or an optical disk recorder. These images can be displayed later in juxtaposition or in superposition and processed for further analysis.

In preferred embodiments, the system includes an image receiving device that includes a microscope with at least one beam-splitter. One output from the beam-splitter provides a visual image, while another output is filtered to pass only photons of a characteristic wavelength, phase, or orientation as a result of the activity. These images are preferably recorded with cameras with frame sampling times and rates synchronized by a common timing device. The cameras may operate at the same video field and frame rates or at integral multiples of such video field or frame rates to achieve increased temporal resolution for a given spectral band or other optical property of the specimen being observed, or to accommodate special image and information display devices. The image at the back focal plane of the objective lens may be directed to any camera in the system with a Bertrand lens or similar device to provide the diffraction image of the specimen.

The data is digitized and then processed and analyzed by an image processing system that may be at the site of the activity or remote. The image processing system is programmed to analyze the image data, and to store and classify signals to establish spatial and temporal signatures of the observed activity. These signatures are accumulated and stored together to provide a library of signatures. The observed activity can be displayed on-line and can also be continuously compared with the signatures stored in the library to determine a correspondence or correlation as an activity is progressing. Variables that affect the activity, such as chemicals or other conditions such as heat or light, can be modified to control that activity while the specimen is under observation.

In an exemplary application of this system and process, a visible image is that is that of a reproductive division of a cell (mitosis) produced by a microscope, e.g., with a signal influenced by changes in the localized refractive index as revealed through the use of polarized light or through methods of phase contrast enhancement, such as phase contrast, differential interference contrast, or modulation contrast optics. Another image indicates an interaction of specific ions or other compounds, such as calcium, with an ion-sensitive photonic reporter or other suitable means. Thus, a spatial-temporal image of photons attributable to and indicative of the presence of particular ions or other components at a characteristic concentration is recorded during mitosis.

In this example, further processing preferably includes rendering the calcium-dependent photon spectrum visible to the human eye with a color assigned to the signals detected by the camera whose input spectral band is tuned to detect the photonic reporting of calcium by the interaction of a calcium specific reporter molecule and a calcium ion. A single color may be used, or it can be varied to reflect at least one of a number of factors including a duration of the photon emission from a particular locations, a temporal or spatial frequency of photon emissions relative to each other, and/or specific structural, chemical, or physical features or events in the cell. The emissions are preferably displayed in an overlying manner to show the locations and time durations of the emissions during mitosis.

The present invention allows a user to understand the role of any component or components and its relationship with one or more other components in an image by studying the dynamics of the interactions of these components and processing and analyzing the characteristic signals of several different signals and their interrelationships during the course of the activity being studied, i.e., in real-time. Such processing and analysis permits more expeditious assimilation of information for the observer, and permits an observer to manipulate a subject and monitor the effects of such manipulation during the course of the observation. The invention provides for comparisons among spectra; for analysis of the relationships among various spectra or spectral bands in any combination of parametric axes; for comparison between simulations of data and system under study; and for analysis of relationships among various spectra and various kinetic simulations and other computational models of the data and system under study, in any combination of parametric axes. Accordingly, the invention is a powerful system and method for analyzing processes subject to multiple spectra. Other features and advantages will be apparent from the following detailed description, the drawings and from the claims.

DETAILED DESCRIPTION

The present invention relates to a system and method for image analysis, and is particularly useful with a microscope system for observing biological processes. While a biological example is described in detail, the invention has broad applicability to other physical, chemical, and biological activities, and can be used on a microscopic, endoscopic, or long-range basis.

Figure 1:
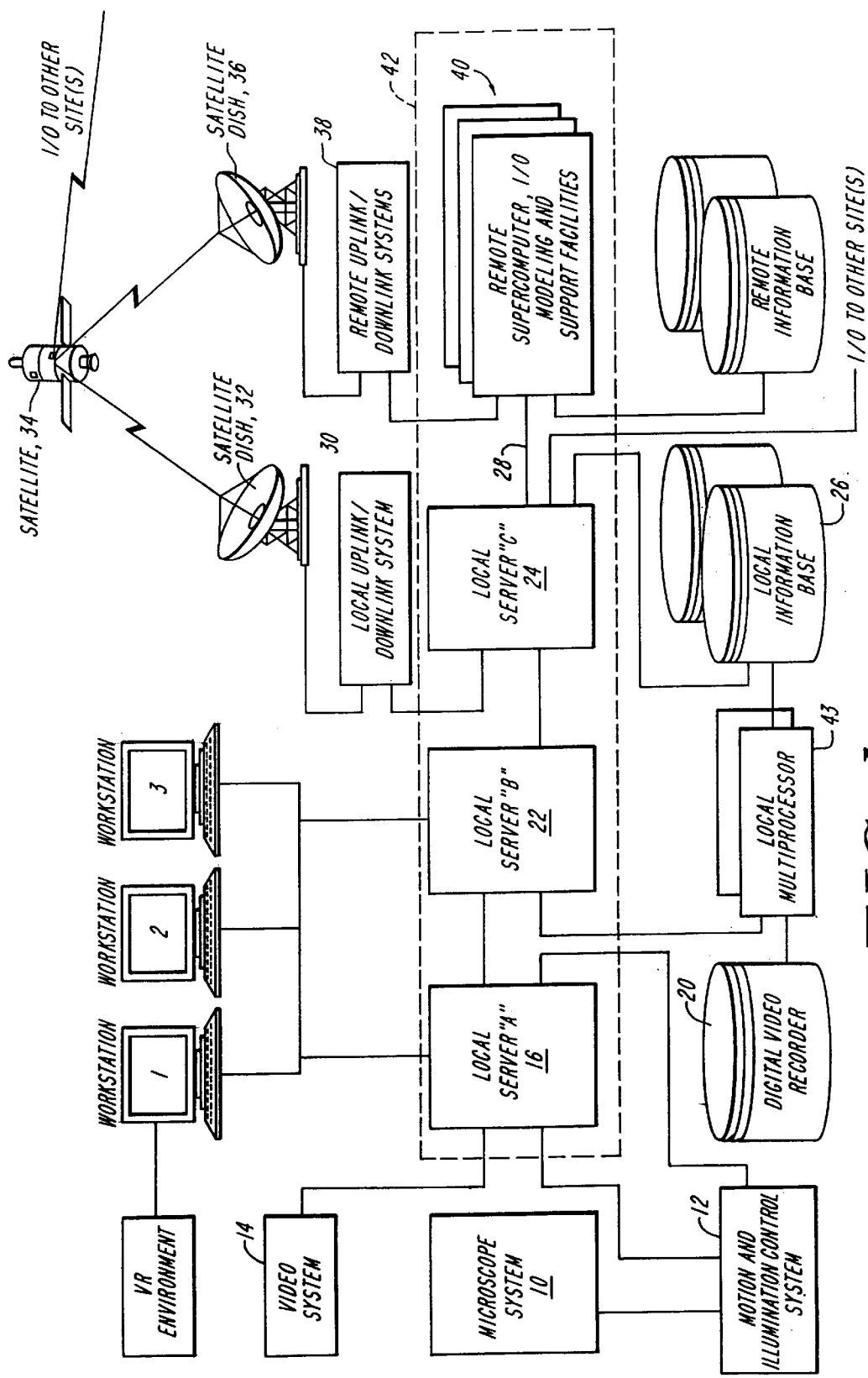
FIG. 1 is a pictorial block diagram of an imaging system according to the present invention.

Referring to FIG. 1, a specimen is observed with a microscope system 10 under control of a motion and illumination control system 12. Microscope system 10 provides images to a video system 14 that captures and records data from the specimen, including at least visual data and point emissive spectral data. The microscope may be equipped with a Bertrand lens or similar device and a beam steering device to direct the image at the back focal plane of the objective lens to any camera in the system to provide the diffraction image of the specimen in a given spectral band.

Video system 14 provides the data to a first local server 16, which digitizes the data and causes digital images to be stored in a digital video recorder 20. Server 16 also provides the digital images at a high rate of speed to a second server 22, which performs image analysis and provides the analyzed data to a third server 24. Server 24 is primarily responsible for data compression, for archiving in a local information base 26, and for transmitting data to a remote supercomputer system or systems 40 for processing. This transmission can be through a hard-wired line 28 or via a local uplink/downlink system 30, a local satellite dish 32, a satellite 34, a remote satellite dish 36, and a remote uplink/downlink system 38.

Taken together, servers 16, 22, and 24, and remote supercomputer system(s) 40 can be considered an image processor 42. While the functions of the image processor are allocated in a particular way with certain local and remote tasks, these various functions can be combined or allocated in other ways, and can be performed with other shared resources, such as a network of workstations.

A local multiprocessor 43 may be used to process and analyze images immediately upon acquisition, to perform post-acquisition analysis, and to display images. Such a local multiprocessor can permit computational processing, analysis, and control functions when the time delays due to velocity limits and bidirectional information transfer imposed by the distance separating the microscope and the remote processors would be intolerable for the process being studied. Such a local multiprocessor could be a Princeton Engine, which is available from the David Sarnoff Research Center in Princeton, N.J., or a Princeton Engine connected via a HIPPI interface to a supercomputer or cluster of workstations.

Figure 2:
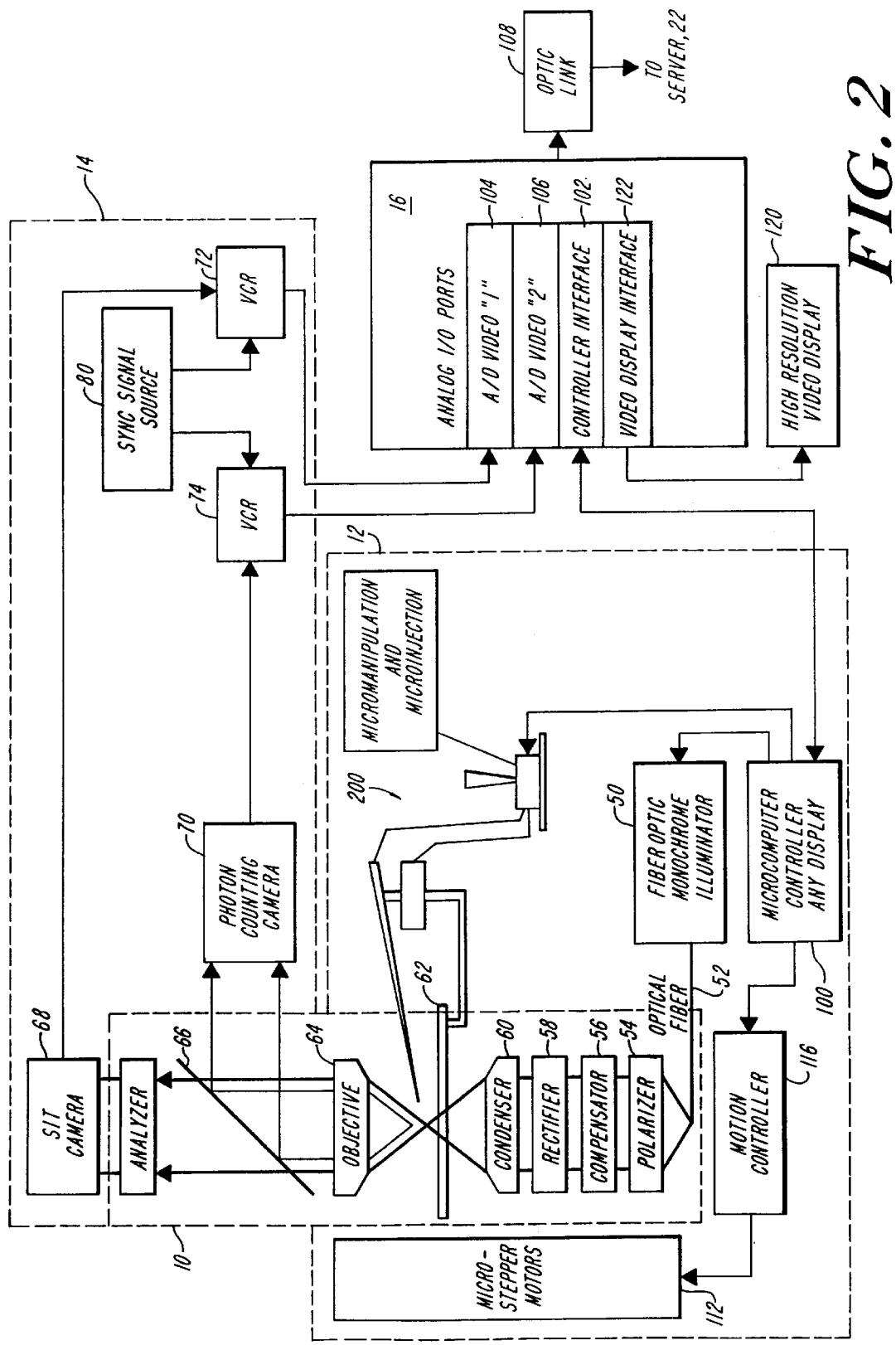
FIGS. 2–3 are pictorial block diagrams of components of FIG. 1 shown in more detail.
Figure 3:
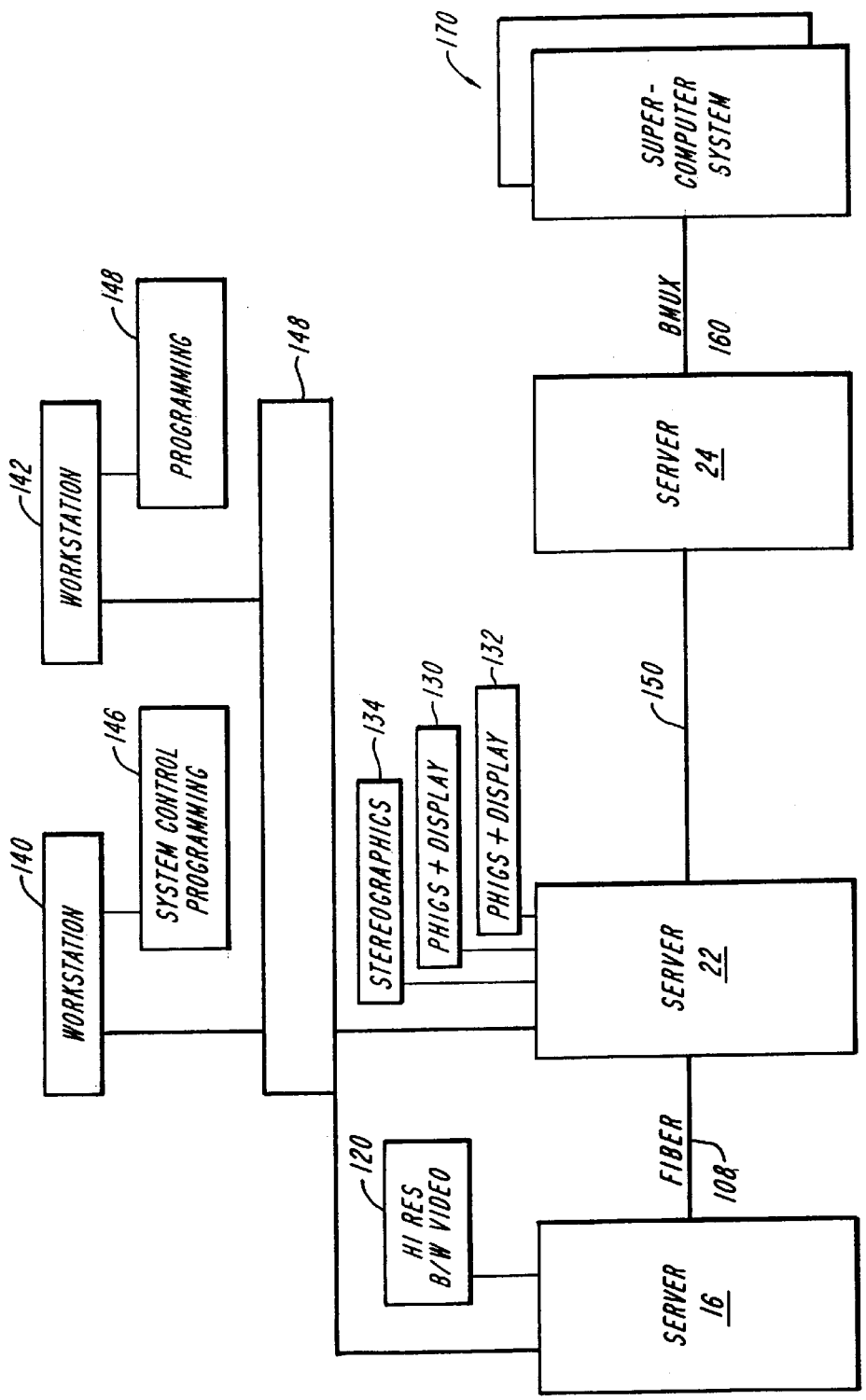

FIGS. 2–3 are block diagrams that illustrate the components of FIG. 1 in more detail. While the system shown here is a two-camera device, other cameras and sensors can be provided for recording additional information by using additional beam splitting. Referring particularly to FIG. 2, microscope system 10 and control system 12 include a microto scope controlled by a microcomputer controller and display 100 via an interface 102 in server 16. Server 16 and controller 100 control illumination, focusing of lenses, filters, motors, and other controls that can be mechanically, hydraulically, pneumatically, magnetically, or electrically is driven, to manipulate light incident to or emanating from the specimen under study.

Controller 100 causes a monochromatic source 50 to generate light with a single wavelength preferably a fiber optic monochrome illuminator, in a well-defined spectral bandpass. The source may include a monochrometer and a bandpass limiting adjustable slit, a special bandpass limiting interference filter, or a similar device. The light is optically coupled through an optical fiber 52 to a polarizer 54, and the resulting polarized light is provided to a compensator 56, a rectifier 58, and a condenser 60 lens. The resulting light illuminates an underside of a transparent stage 62 on which rests the specimen under study (not shown).

The end of the illuminating fiber, and thus the point source of light for the illumination of the specimen, may be provided with a further device (not shown) for positional control to permit positioning of the point source of light at alternating positions synchronized to the scan rate for video frames or fields, thereby providing oblique illumination and generation of stereoscopic images using a single objective lens and a single condenser lens.

An objective lens 64 receives an image of the specimen during the activity and provides the image through a beam splitter 66 that directs the image to two separate and different cameras 68, 70. Camera 70 is preferably a photon counting camera, such as a model made by Hamamatsu Photonics, and camera 68 is preferably a silicon intensified target (SIT) low level light camera that captures a differential interference contrast (DIC) image of the activity illuminated with the light generated by source 50. Other cameras and beam-splitters can be provided to receive further images, such as a second photon counting camera.

An infrared camera can also be provided to detect thermal emissions and to produce a thermal signature of the activity. The infrared camera allows assessment of the infrared absorptive and emissive properties of the specimen being observed. Such thermal emissions are a function of the physical activity of the specimen in an emissive region, including changes in temperature associated with changes in chemical, electrical, and/or physical activity, rates of reactions or changes in concentration of particular components or classes of components of the specimen, or other thermodynamic properties of the specimen. The infrared camera is positioned at an optimal location for detection of image information in the bandpass of interest. The optics of the microscope may be fabricated from infrared transmissive or reflective materials, such as germanium, germanium composites, or gallium composites, properties that are compatible with the conditions of the observations being performed.

Cameras 68, 70 receive analog data and provide the received data to respective VCRs 72, 74 to be recorded. The VCRs are driven by a common external horizontal and vertical sync signal source 80 at the level of full video frames and preferably corresponding video image fields (e.g., using subcarrier phase locking), and are preferably equipped with SMPTE (Society of Motion Picture and Television Executives) time code generators operated to insure sequential numbering of all video frames in a manner that provides temporally accurate time references among and between sets of original recordings. This numbering expedites the registration of multiple image sets. The SMPTE time code generator may also be set to operate on a time signal provided by an external standard, including the Global Positioning Satellite system.

The signal path for one or more of the VCRs may be equipped with noise reduction devices to reduce the noise to level in the signal, and a VITS (video information test signal) and VIRS (vertical interval reference signal) video standard reference signal generator to provide a set of standard reference signals in image space not used by the detector faceplate of the camera. Such reference signals is insure accurate reference of recorded signals at each set of transmission to downstream video image reception points. With such a microscope and camera system, multiple concurrent images of the specimen can be captured and recorded.

The visual and emissive data provided from VCRs 72, 74 is provided to first server 16 for preprocessing to permit temporal or spatial noise to be filtered, and to permit the extraction of features of interest and importance to the understanding of the activity being observed. Server 16 has two analog to digital (A/D) conversion units 104, 106 for receiving and converting the received analog data into digital data suitable for initial processing and/or for transmission to other servers.

First server 16, which is preferably a reduced instruction set computer (RISC), such as an IBM RS/6000-540, or a high performance personal computer with high computational power. Server 16 is equipped for video-rate input, throughput, and output at a rate equal to or in excess of 50 megabytes per second, and is optimized for real time, interruptdriven I/O activity. Server 16 sends digitized images via high speed fiber optic link 108 to second server 22. In the RS/6000, for example, the microchannel ports and bus speed allow a total of four video input sensors, as well as one channel to control other features, such as focal plane motion and shutters.

In addition to acquiring and digitizing images, server 16 controls any microstepper motors 112, shutters, filter wheels, a motion controller 116, and other devices associated with primary imaging activities via controller 100. Actuation of microstepper motor 112 alters the microscope (e.g., focus, focal plane axis, orientation, thickness, X-axis, Y-axis, Z-axis, and rotational stage movements) and the optical configuration (e.g., DIC, POL, lens or filter or other modulator position, orientation and/or actions, or stereoscopic). The user preferably controls these functions from one of workstations 140, 142 (FIG. 2) by selecting icons with a pointing device, such as a mouse or a trackball. Because the activity and the analysis thereof can be observed in real-time, a user can make changes from his/her workstation during the activity.

Server 16 can be programmed to initiate motion control of the microscope in response to particular sequences or patterns of activity. One such computer-initiated response changes the microscope's focal plane in discrete timedependent steps, cycling from top to bottom, then returning to the top surface of the specimen. Such images provide information for tomographic reconstructions in low to moderate resolution in support of on-line experiments, and at high resolution in post-acquisitional analyses. Server 16 also has a video display interface 122 through which images and other information can be displayed on a high resolution video display 120 that can be color or monochromatic.

Server 16 may also record the coordinates for each position at which the microscope is set to record and later study the path of viewing of a given specimen during a given observation, to optimize the path for future observations, or to reconstruct the shape of a specimen following a tracing of the structure using the focal point as a probe of the surface features of the specimen.

Referring to FIG. 3, second server 22, which is also preferably a computer similar to that used for server 16, serves as the primary local unit for image processing, analysis, and interactive graphics. Server 22 performs arithmetic, logical, and interactive imaging functions, such as rotational reorientations and three-dimensional polygon to rendering, i.e., the interactive visualization and manipulation of complex shapes, preferably facilitated by a resident graphics program such as PHIGS+or HIDEM, within the hardware of server 22. In addition, server 22 provides images to graphics monitors 130, 132 to present to dimensional images for each video sensor, as well as a display 134 for stereoscopic projections and tomographic constructions, such as a StereoGraphics Z-screen, a CrystalEyes display, a holographic display, a viewer mounted heads-up display, or a high resolution three-dimensional display. Server 22 preferably has a higher level of computational, processing, analysis, and display power and memory than server 16 to permit bitmap animations and to control the graphics monitors and the display.

Two graphical workstations 140, 142, linked via a network 144 to servers 16, 22, are equipped with software modules 146, 148 for system control and data management during simulation experiments, and for programming and systems management. Thus, programming personnel can participate directly in an experiment by redirecting computational analyses during the course of an experiment or helping to address 'what if' questions. Microscope system 10, servers 16, 22, and workstations 140, 142 are all preferably located at the site of activity under study.

Server 22 provides data over a transmission line 150 to a third server 24, preferably also a RISC computer, which is programmed for data compression, for archiving in the library of signatures, and for database management. Server 24 uses a direct block multiplex (BMUX) channel 160 or other suitable wide channel line connection to a remote supercomputer system 40. The use of such a line that requires that server 24 be in close proximity to supercomputer system 40, permits on-line use of the supercomputer's multiple processors for computationally intensive activities, including three-dimensional and tomographic visualizations, intra- and inter-video sensor relational kinetics and pattern analyses, computational models, and kinetic simulations. Such proximity may be extended with suitable high speed, broad bandwidth digital information transfer methods.

Supercomputer system 40 may consist of one or more high performance computational engines, such as a massively parallel computational engine, such as a 1024-processor or 2048-processor Princeton Engine. The supercomputer system may be designed to use electronic and/or optical processing of images and may be of a SIMD or MIMD architecture, using processors operating synchronously or asynchronously, or in various combinations of the above. Depending upon its design architecture, operating system, size, and capability, this system can enable the user of the system to perform analysis at high levels of sophistication. System 40 may be located at the same site or distributed over a number of sites with appropriate communications. The harnessing of the various computational engines may be predetermined by the operator or determined during the course of a particular application or process by the operator or by one of the computational engines by using an algorithm designed to assess computational activity and needs and to recruit needed and appropriate hardware and software resources from among local and remote sites during the course of an application or process using the process described herein.

The powerful processing system 40 allows numerous and sophisticated image processing applications and analysis to be performed. The analysis preferably includes at least comparing visual signals to signals representing point emissive data, and correlating these signals. The data may also be manipulated and digitally or optically filtered; for example, the data may be sampled at periodic intervals to determine if there are periodic characteristics to the point emissive data that can be classified and distinguished as a particular type of signal or as a noise of a particular variety. The point emissive data can be filtered to remove random noise and to remove data generated from background emissions and not related to the emissions caused by the activity under study.

With remote processing, when the visual and point emissive data are processed, the results are transmitted to the site of the observed activity via communication links. These results are stored in local information base 26 in a signature library for later study and for comparison with new activity data. During operation, the image processor produces signatures for an activity under study, retrieves signatures from the signature library, and compares the signatures of the activity under study to the signatures stored in the signature library. If there is a match, correspondence, or correlation between the signature under study and one or more signatures stored in the library, the image processor can transmit information about such a correlation to the display unit in real-time.

The processing performed by the image processor preferably includes computational edge detection and enhancement procedures "on-the-fly." For edge detection of a specimen, gray scale values of edges are determined, all other gray scale values are removed from the image, and the remaining background values are brought to a common, intermediate value. This procedure results in a dark curve representing the edge of the object(s) of interest on a neutral or gray background. A low pass spatial filter is applied to minimize the effects of imaging aliasing thereby computationally sharpening the image.

Further, for a given activity, how much spatial temporal patterns may change during a cell cycle under normal or abnormal activation can be determined. Analysis of diffusion, refractive index, or other physical, chemical, hydrodynamic or other properties or processes of the specimen under study can be performed.

Visualization is achieved by optically sectioning the specimen followed by three-dimensional (3D) reconstruction. The system translates each object within an optical section into a digital contour. Image reconstruction involves identifying contours of each object and connecting those two-dimension (2D) contours to form 3D shells. The optically determined shape of the specimen serves as the framework within which other images (such as flashes of light of aequorin luminescence as discussed below) will be located by superposition of the real-time data onto a 3D model. From this reconstruction, the image processor synthesizes a left and right eye view of the specimen. By displaying these two slightly differing images, one to each eye, stereo perception can be simulated on the computer screen so that the image of the specimen appears truly 3D.

Sound can also be used to produce auditory cues to aid in the perception and recognition of spatial and temporal patterns of the luminescence signals. Separate tones and pitches can be assigned to each position of the video sampling grid, and such tones and pitches can be output as detectable sound in monaural or stereoscopic formats. Such image information dependent audible output may serve to assist the observer in detecting patterns of structure and/or activity, as well as changes in such patterns of structure and/or activity.

Observations can additionally be recorded on an audio track of the videotapes by using a microphone connected directly or indirectly to the video tape recorder or other recorders. The SMPTE time code recorded simultaneously on an audio channel or other suitable recording channel separate from that used for voice recording can be used to insure accurate video frame registration of image information among each separate spectral band and of combinations of spectral bands produced in analog and/or digital modes during or subsequent to the initial observation. In addition, a VITS signal can be introduced into the recording path of one or more separate video channels to insure that, following standardization of video system performance (e.g., black and white levels, color bars, black burst, VIRS, etc.) prior to the beginning of each recording or observation, the signals received at remote locations can be adjusted to compensate for losses and noise incurred during transmission of the video image and other signals. At times it may be useful to check the video system standardization during an observation or series of observations and analyses to insure that no deviation, gradation and/or drift has occurred in those values. In such cases it is the preferred practice to monitor the on-line performance of the video systems with a video waveform monitor and other such devices. Other data, such as that from recordings of cellular activity may be recorded to other available channels on the video tape or other recording medium.

EXAMPLE—CALCIUM ION CONCENTRATION DURING MITOSIS

Some of the capabilities and options of the system of the present invention are described in more detail by way of a particular example.

All living organisms are composed of cells which reproduce through mitosis, a well-known and widely-studied process by which a cell reproduces by dividing itself into two or more cells. During mitosis, there is a change in distribution of protons found inside a cell and of intracellular free ions, such as calcium. It has been found that the concentration of intracellular free calcium ions undergoes subsstantial changes prior to, during, and after mitosis. Some studies indicate that the ion concentration of calcium may be a cause of, or at least closely correlated with, the control of mitosis and other processes of the cell.

The division of one cell to two cells is clearly visible with a microscope. Moreover, variations in a level of calcium during cellular activity can be detected because photons emitted by a luminescent calcium-sensitive reporter are emitted from cells that are labelled with the reporter.

The approaches and methods described herein may also be applied in those cases in which it may be useful to use a fluorescent calcium-sensitive reporter, such as fura-2 or calcium green, to follow such changes in calcium concentrations in cells. When fluorescent reporters are used to analyze the distribution of calcium ions computational methods should compensate for the effects of diffusion of the calcium-reporter complex and for the buffering effects of the reporter on local concentrations of calcium ions. These emissions follow patterns that have both spatial and temporal signatures; i.e., the cell releases calcium ions from intracellular stores which concentrate in particular places called microdomains within the cell. The localized concentration of calcium ions varies over time. Calcium ions may be controlling factors or may be transmitters of controls for regulating the process necessary for controlling mitosis.

Figure 4:
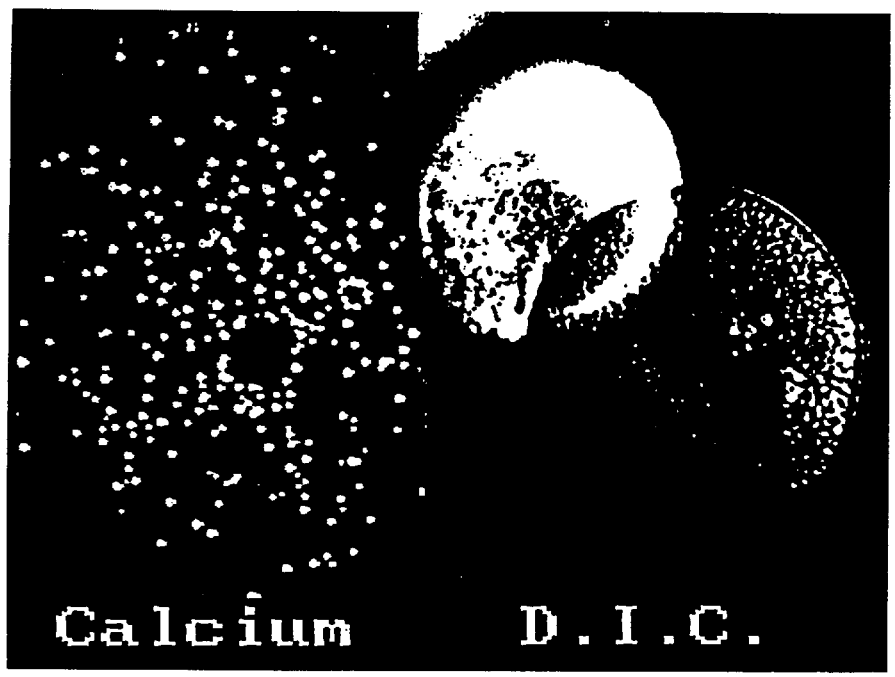
FIGS. 4(a)–4(c) are images produced according to the present invention.
Figure 4:
Figure 4:
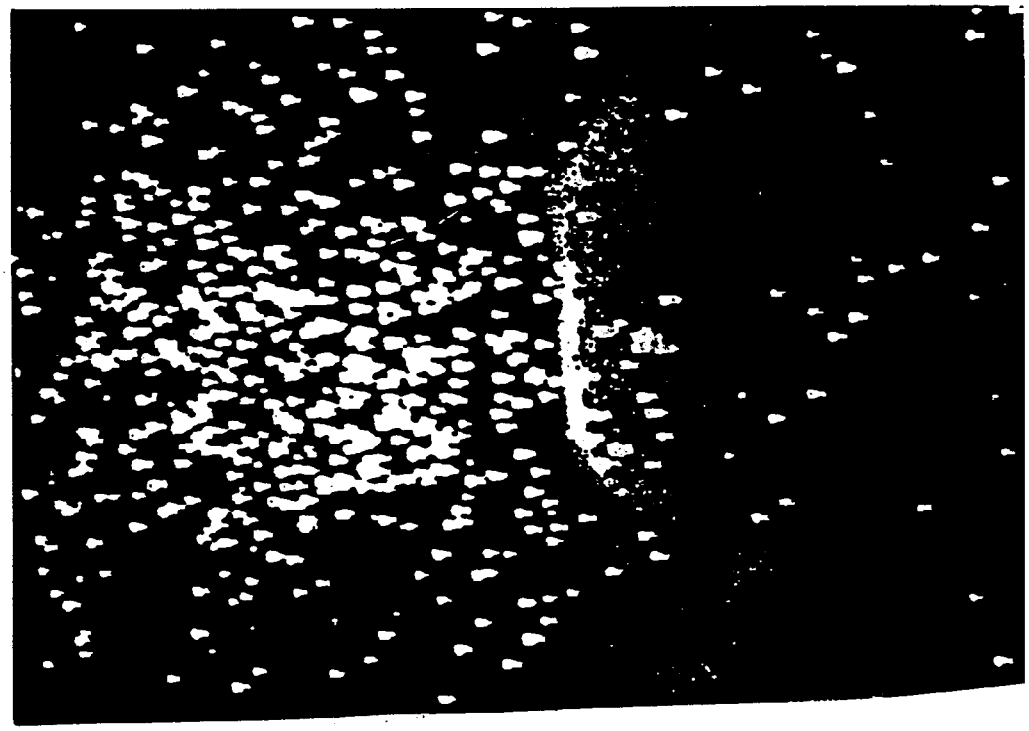

FIGS. 4(*a*)–4(*c*) are exemplary photographs showing, respectively, (*a*) images representing calcium ions and cell division side-by-side; (b) images representing calcium ions and cell division superimposed; and (c) simultaneous capture of images representing calcium ions and cell division.

In this exemplary embodiment, the specimen includes a cell disposed on a transparent microscope slide. Referring again to FIG. 2, a micromanipulation and microinjection sysem 200 can be used to inject into the cell quantities of one or more samples for use in observing the cell and its activity. Such microinjection is a well known process. By following the electrical properties of a cell using electrodes that measure the flow or waves of ions, electrons, or other charged or uncharged particles across membranes of the cell, cellular activity may be observed by following changes in localized concentrations or displacement of charged or uncharged particles using one or more electrodes specifically designed to measure such localized concentrations or displacements of particles or waves outside the cell.

The microscope allows the cell or a portion of the cell to be illuminated with a quantity of light. Cellular activity or photolytic release of a compound or compounds that may or may not influence cellular activity can then be observed. Known processes may include the photolytic uncaging of reagents, fluorescence photobleaching, fluorescent recovery after photobleaching, imaging and/or manipulations using acoustic wave energy, laser-mediated ablation, manipulations with high energy particles such as alpha particles or x-rays the use of laser tweezers, and the use of laser scissors. Such manipulations may be under the control of the computer system with motion and illumination control system 12 interacting with, and directed by, local servers 16, 22, and 24, local multiprocessor 43, and remote supercomputer 40, to provide for spatially and temporally accurate manipulations of the specimen. Those manipulations may be the result of the computer system recognizing new or previously catalogued information within patterns observed from the cell, and/or other instructions provided by the observer. During mitosis, calcium ions and other particles are observed at the locations at which the concentration of such particles may be determined at various locations within the cell.

Aequorin, a luminescent photoprotein from the jellyfish Aequoria, serves as a calcium reporter because it emits a photon upon the binding of one $Ca^{2+}$ at a particular intracellular free calcium ($Ca^{2+}_i$ concentration, and provides graded sensitivity to different concentrations of $Ca^{2+}_i$ as a means of bit-slicing through $Ca^{2+}_i$ concentration levels, and displacements and/or changes in $Ca^{2+}_i$ concentrations. The luminescence of aequorin appears as discrete flashes on an otherwise dark background. While some regions of a cell have repeated flashes, other regions appear dark for all but stochastic emissions from the cell or shot noise from the imaging and recording system.

$Ca^{2+}_i$ signals are localized in time and space. Based on a timing resolution of 30 Hz video circuitry, it appears that individual $Ca^{2+}_i$ flashes have a lifetime of less than 100 msec. Typically, a first video frame contains the maximal signal and subsequent frame intensities are linearly reduced to background within two additional frames.

$Ca^{2+}_i$ transients are clustered within the cell: while some regions of the cytoplasm are very active, others appear to be dormant. Rapid photon pulses or bursts are observed around the nucleus before nuclear envelope breakdown (NEB). Discrete, rapid emissions are found localized in the mitotic pole region during mitosis, and low frequency, high amplitude emissions are seen at the site of the contractile ring immediately before and during cytokinesis.

Experimental results indicate that there is a physiological link between a temporally regulated transient elevation in $Ca^{2+}_i$ and the control of mitotic events. Thus, it is important to determine if concentration of $Ca^{2+}_i$ increases in association with the events of NEB and the onset of anaphase during which time the chromosomes are segregated to the daughter cells. Aequorin in one of a number of forms can be a usable reagent for the study of $Ca^{2+}_i$ in dividing cells.

When a two-camera system as shown in FIG. 2 is used for studying dividing cells, each camera provides video pixels at a resolution preferably corresponding to a square of 500 nm per side. A resolution of about 365 nm compares favorably with the maximum limit of spatial resolution (ultimately resolution=$f_c$=(0.5)(wavelength)/NA) attainable at a standard 546 nm working illumination for microscopy. Because brightness decreases with magnification, doubling the magnification of the objective lens decreases brightness by a factor of four (holding NA constant). The microscope preferably uses a Nikon plan apochromatic 20X/0.75 NA objective lens, which has a brightness rating of 14.0625. In some circumstances it is preferable to use a Zeiss plan apochromatic water immersion 40X/0.75 numerical aperture objective lens, which has a brightness rating of 3.156. Optically, the image of a cell is preferably formed with a set of high performance, rectified differential interference contrast (DIC) or polarized light (POL) optics. These lenses enable one to optically section a living cell into very narrow image slices, with minimal interference from out-of-focus images. Images are preferably detected with an SIT camera and a dual microchannel plate intensified saticon tube camera for indicating the incidence of single photons on a target.

Mechanically, the microstepper motor driver controls the stage and focus to allow precise positioning of the vertical focal plane to within a single focal plane step of 31.5 nm (+/−0.8% over 6×10$^5$ steps), and 100 nm horizontal specimen plane. A digital microstepper motor driver, controllable through a microcontroller, permits remote operation, a capability that is essential for single photon video observations.

The image processor controls data acquisition, processing, analysis, and support with software residing in the computer, and also controls, directly or indirectly, hardware for the A/D conversion of the signal or sequential, full-frame video frames from each camera sampling spectral bands, and the recording of such images in digital format such as video disk recorders, clustered magnetic hard drive arrays, or other such devices. The system preferably permits digitization of such video signals to 10 bits per byte of data and permits transmission of the image information as a digitized signal over appropriate communications pathways. Such a system also permits the D/A conversion of the image information for playback and transmission. Software drivers and other tools are provided for performing quantitative, real time, matrix-based regional subsampling of the intensity of video images.

Examples of software tools for a personal computer system may preferably include tools for (1) digitizing the image brightness of a 10×10 rectilinear sampling grid of one hundred contiguous 5×5 pixel subregions; (2) summing the photonic intensity of each of the box subregions plotted against time in a 10 by 10 array; and (3) producing a gray scale rendition of the files from the summing program. The playback rate ranges from one frame per second (33 msec of recording time) to single frame readout of selected frames.

The development of luminescent and fluorescent probes for intracellular chemical events permits the study of cellular regulation at the level of the single cell. Due to the photon emissive properties of individual reporters, as well as the absorption properties of the cells to be studied, one can follow at least two different chemical pathways in a single cell. For instance, $Ca^{2+}_i$ is monitored in a cell microinjected with aequorin, at the same time ATP concentration or alkaline phosphatase activity will be monitored in the same cell also microinjected with luciferase and appropriate luciferin analogues. Quantitative imaging of other cellular properties is possible.

Table I is a list of cellular attributes that can currently be imaged:

TABLE I

Reaction or Process
Bio-luminescence and chemi-luminescence
Intracellular free $Ca^{2+}$ concentration
Alkaline phosphatase activity
Intracellular reduction-oxidation potential
Conventional illumination methods
Microtubule assembly
Nucleus and other cellular organelles
Fluorescent probes
Quantitative Imaging Mode
Aequorin/photon counting
Aequorin/ratio photon counting
Luciferase/photon counting
Luminescence/photon counting
Luminescence/superoxide production/photon counting
Luminescence/adenosine triphosphate (ATP) production/photon counting
Luminescence/translation of messenger RNA yielding peptide and protein production/photon counting
Luminescence/transcription of messenger RNA as a determinant of gene activity/photon counting
Birefringence, POL and DIC (transmission and/or reflective optics)
Specific/selective intracellular ions (e.g., calcium, magnesium, potassium, chloride)
Phospholipase A2
Phospholipase C
Intracellular pH
Voltage potential across membranes
Mitochondrial distribution
Endoplasmic reticulum distribution
Distribution of Golgi bodies
Distribution of nuclei and/or other organelles and structures
Acidic endomembrane organelles
Chromosome replication, condensation, movement
Lipid analogues/fluorescence
Lipid fluidity and metabolism
BCECF/fluorescence
Voltage sensitive fluorescent dye
Rhodamine 123/fluorescence
Di-i dyes/fluorescence
Acridine orange/fluorescence
DNA/vital dye fluorescence
Protein kinases and/or phosphatases
Proteolytic enzyme activity
Cytoskeletal components (e.g., actin, tubulin, myosin, dynein, kinesin, etc.
Adenosine triphosphate (ATP)
Cyclic adenosine monophosphate (cAMP)
Fluorescent molecules
Fluorescent derivatives of molecules and/or other bodies
Fluorescence energy transfer within molecules and/or other bodies
Fluorescence energy transfer among molecules and/or other bodies
Diffusion or other translocation of ions, molecules and/or other bodies
Heat emitted due to chemical, molecular and/or other activity
Changes in molecular or other level(s) of physical and/or chemical organization and orientation The SIT or intensified CCD low light level camera captures a DIC image of a cell illuminated with 710 nm light projected through a condenser lens to an objective lens. The photon counting camera sees the 465 nm photons emitted from a $Ca^{2+}_i$-dependent aequorin reaction. A second photon counting camera can be used to see photons emitted from the cleavage of specific luciferin analog within the 500 nm to 580 nm range, e.g., for ATP or alkaline phosphatase, by the luciferin luciferase (fire-fly tail) reaction. A fourth or further sensors can be added if the bandpass of a third reorter (luminescent or fluorescent) is within a trough of the other three illumination modes. The target phosphors routinely used in the photon counting cameras, while optimal etween 450 nm and 550 nm, render these cameras "blind" above 650 nm, thereby facilitating the use of 700+ nm light for DIC and POL visual images.

Multiple concurrent images of the cell can be produced including one showing the whole cell organization; a second showing $Ca^{2+}_i$; and a third showing where another activity is located. The analog output signal of each camera is recorded on a respective VCR, and then is sent to a first computer of the image processor. These images form high resolution tomographic reconstructions in post-acquisition analyses, or low to moderate resolution in support of on line experimentation. Real-time digital mixing of the image records from individual video sensors permits superimposition of the signals due to $Ca^{2+}_i$ of other visualized parameters upon structures within the cell, and perform on-line relational analyses of $Ca^{2+}_i$ and other intracellular regulatory events in normal and experimentally manipulated single cells.

To take full advantage of the quantitative nature of aequorin luminescence, a detailed statistical analyses is applied to the emission patterns of activities. One use of the invention is to determine the spatial and temporal frequencies of $Ca^{2+}_i$ for each region of the cell, and to correlate these patterns with particular features within cells (e.g., nuclei, mitotic poles, cleavage furrows). In this way one may move 2D imaging over time from a semiquantitative or quantitative form to quantitative and relational forms. Pattern analysis algorithms stored by the image processing system are applied to the video image records to discern geometric relationships (i.e. bilateral spatial symmetry, spatial branching, and temporal patterns) within the image sets.

The imaging system generates a set of rich visual imagery at a very high rate. Depending upon the application, the relevant information to be analyzed may be temporal, 3D, or multispectral, and may involve correlating data from several different imaging sensors. A portion of this system involves the standard computer vision techniques that have been established. Standard software exists and for analysis of multichannel image data (e.g., maximum likelihood classifier, clustering procedures), temporal image patterns (e.g., Fourier transform, change detection procedures), and spatial patterns (e.g. 2D Fourier transforms, geographic information systems). These tools can be merged and optimized to create a combined spectral, spatial, and temporal pattern analysis procedure. Such programs may be run on clustered workstations or supercomputers.

In each half of a dividing cell, for example, the edge of each object visualized in one spectral band different from that used for calcium showing calcium-dependent emission capabilities exhibited by aequorin-base luminescence as visualized in the aequorin luminescence spectral band, may be superimposed onto pairs of Cartesian coordinate planes using the mitotic poles as the origin. The X-axis is described by the pole-to-pole axis, the Y-axis is projected through that pole and is perpendicular to the X-axis of that cell), and the Z-axis is parallel to the optical axis of the imaging system, the objective lens. The edges of some structures to be imaged will not always remain confined to the optical plane of each observation. In such cases, the system tracks particles as trajectories following an initial curve to allow one to extrapolate across discontinuous portions of the particle's path due to optical-mechanical distortions in a cell and meandering within and outside the depth of field of an image plane (e.g., 1.2 micron thick) used for initial image acquisition. Such "filled-in" trajectories will then be recomputed to provide the best possible fit for the edge. By using appropriate tracking and multidimensional curve and surface fitting software on a cluster of workstations or a high performance computational engine, an equation that best fits the curve form through iterative curve fit algorithms can be determined. Such computational analysis of image data is used to solve for surface topography of isosurfaces depicting cellular or chemical activities and object spatial deformations and displacements over time.

A variety of UNIX-based X-window display environments can be used for 2D and 3D data plots and other computational visualizations such as simple X-Y plots, histograms, surfaces, and volume renderings. Shaded polygon images are possible with a graphics environment and graphics engine, preferably with hardware residing on one computer and software on another. Wavefront software on the computers produces credible images, and is currently used to make videotape for both local and remote users. Still images can also be displayed in an X-windows environment. A form of X-movie displays Wavefront frames on a workstation screen fastener enough to preview animation and can be sent to remote users by fast mail. A volume rendering program can be used to convert 3D data sets to surfaces. The resulting images can be displayed in X-windows or another suitable format, or saved as a compressed raster for later display in an X-window for transmission to remote workstations.

With sufficient network bandwidth, the intermediate videotape step can be omitted and animated sequences can be constructed directly on an intermediate video rate memory device, such as a video disk recorder, optical memory disk recorder, or RAID memory disk array, and then displayed on the screen of the user's workstation.

One benefit of the system is the development of a 3D volume rendered virtual mitotic cell (including intracelular organelles and other compartments) constructed from real time tomographic data and multifaceted in vivo and in vitro experimental data. This virtual mitotic cell will, in turn, be subject to computational experimental manipulations of a wide spectrum of cell physiological and biochemical (molecular and ionic) parameters associated with mitosis and the cell cycle.

Large intracellular structures limit the diffusion of articles such as $Ca^{2+}$ throughout the cell. These structures can affect interaction with other intracellular reactants such as $Ca^{2+}$ dependent enzymes. If those reactants are transiently bound to intracellular membranes, the chemical kinetics of the reaction can be very complex. The complex 3D geometry of the reaction space make this kinetic problem a prime candidate for the use of Monte Carlo modeling techniques, including discrete Monte Carlo modeling techniques. The Monte Carlo method for solving chemical kinetics problems has a distinct advantage in that 3D diffusion of reactants in a space with complex boundaries is easily handled. In contrast, simultaneous partial differential equation methods for problem solving, which are preferred for 1D or 2D problems having simple geometric symmetry, become extremely cumbersome and inefficient as the number of dimensions and complexity of the bounding surfaces increase. The data sets and number of simultaneous parameters for this problem are so large that only with the use of a supercomputer or clustered high computational powered workstations will we be able to arrive at a solution in a timely fashion.

Predicting cellular and intracellular behavior from various conceptual models thus is greatly facilitated, and the presence or absence of important unifying precepts can be clarified. Candidate models are run multiple times, and a mean model solution.

One application of particular importance for quantal emission photon imaging is analysis of photon scatter and luminescence image noise. One application of this effort is to determine the source of the higher number of photos distributed throughout the image filed, yet outside the boundaries of the labeled cell. These are the result of internal system scattering, that is, a deflection from particles within the cell and from the various surfaces within the entire cell and the imaging systems. Monte Carlo simulations, similar to those developed to model regulation of acetylcholine receptors and ion channels, can help establish a model that describes the ultimate source of these scattered photons.

One imaging system of the present invention can be used to determine the properties of $Ca^{2+}_i$ release, buffering, and re-uptake for various subregions within a living cell. This determination is made with frame-by-frame frequency and amplitude analysis of photon emissions during each experiment. This is a computationally intensive and voluminous extension of the approaches for data gathering, and relies on the supercomputer and available graphical hardware and software.

One may also perform a number of evaluations, including Fourier analysis of integrated patterns, and chi-squared analysis of each subsampled region within an injected and control cell. In addition, imaging systems can be combined to probe the effects of various agonists and antagonists of various metabolic and structural or other activities and $Ca^{2+}$, buffers on the levels and patterns of $Ca^{2+}_i$ lipid derived second messenger, protein kinases and phosphatases, proteolytic enzymes, endonucleases, various mechanism for post-transcriptional and post-translational modifications, and other reactants. Results from these modeling experiences can be compared with in vivo and in vitro probes of the $Ca^{2+}_i$ regulatory system to model the regulation of mitotic processes, and to evaluate various models.

The system performs computational comparisons of image information from experiments with living cells and experiments performed on computational modelings of the system under study with modeling systems operating on computers and workstations such as the object oriented DEEM environment developed by the Argonne National Laboratory. This system corresponds output living cells and computational simulations and indicates likely areas for improvement of the accuracy and precision of the computational model, as well as indicating experimental approaches for studies of living cells. This approach is scalable to specimens other than living cells that may be studied with this system. This approach also provides for establishment of a dialog with the specimen being studied, with the potential outcomes including imposing an observer-deemed manipulation and/or regulation upon the specimen under observation. In such an embodiment, the system would utilize the information obtained through the capture, processing, and analysis of image information, including spatial and temporal patterns of chemical, physical, and other reactions and transformations associated with specific events inherent to the specimen, and utilize that information to direct the regulation of the process occurring, about to occur, or capable of occurring in the specimen. Such an action would take advantage of all elements of the system as described and other components as may be necessary.

An example of such an application would be the use of spatially and temporally regulated generation of intracellular calcium signals, such as those detected with aequorin in dividing cells, wherein the localized elevations of intracellular calcium concentration is achieved by flash photolysis of caged calcium or other caged compounds that would elicit the increase in localized intracellular calcium by other natural or designed method. Such an application can be readily scaled upward to include treatment of tissues, organs, organ system, and entire people, and can be scaled downward to range from single cells to regions of cells and components of cells including organelles, molecules, and groups of molecules.

While the invention has been described for use with a microscope, it can be used on a long-range basis for tasks such as assessment of crops, or environmental and industrial activity. These activities can be analyzed by obtaining images using two or more different spectral bands, and comparing the data contained in each of the images to develop information relevant to the subject under observation. Such images can be obtained from imaging devices located in aircraft, balloons, spacecraft or satellites, and can include the health of a particular crop, cloud formation and other meteorological information that portend a storm or other is condition, state of disease of a forest, chemical composition of smoke emitted from a factory, or the growth state of plants located downstream of a site of effluent discharge into a body of water.

The system can also be used in the field of endoscopy for assessment of the metabolic state of a patient's tissue or organ by measuring photonic spectral properties of that tissue or organ. Specific metabolic parameters of a tissue can be determined directly or indirectly as a function of the absorption of light of particular wavelengths and spectral bands. Similarly, various optically active reporter reagents can be used in conjunction with simple absorption methods to assess other metabolic parameters. In situations of pressing need, such as emergency medical treatment or lapriscopic surgery, an imaging system according to the present invention can provide real-time assessments while visualizing the tissue in question, even during the performance of a surgical procedure.

Having described embodiments of and examples of applications for the present invention, it should be apparent that modifications can be made without departing from the scope of the appended claims. Other applications of the system may include on-line computational steering of biomedical, chemical, and physics experiments, machine directed ophthalmic laser surgery, intrauterine fetal surgery, telesurgery, distant evaluation for tissues and samples studies for diagnostic pathology studies and other practices of telemedicine, evaluation of toxic conditions in an environment, the use of medical imaging technologies such as MRI, PET, and CAT scan for new forms of non-invasive surgical procedures, high energy particle physics, improved real time machine vision for robotics and air traffic control, and inspection, fabrication, and modification of 2D and 3D integrated circuits. The ability to observe cells and tissues can allow processes to be observed and recorded from living bodies, including, for example, effects of toxins or radiation on tissues or cells. The observation of such cells is not limited to animal cells, but can also apply to plant cells, and to other entities.

What is claimed is:

1. A method for analyzing a specimen during an activity, the method comprising:
   recording visual images of the specimen to provide a spatial and temporal recording of the specimen during the activity;
   recording photon images representing emissions of a first photon from the specimen during the activity so that the visual images and the photon images are obtained simultaneously; and
   displaying simultaneously the spatial and temporal recording of the specimen and the photon images so that a user can visually see visual images of the actual activity and images of photons.

2. The method of claim 1, wherein the displaying includes displaying the visual images and photon images adjacent one another.

3. The method of claim 1, wherein the displaying includes displaying the visual images and the photon images in a superimposed manner.

4. The method of claim 1, wherein the recording includes recording the images as signals, the method further comprising a step of processing the recorded signals to determine correlations between the visual images and the photon images.

5. The method of claim 1, further comprising, simultaneously with the recording, recording space and time varying signals representing emissions of a second photon from the specimen during the activity.

6. The method of claim 1, further comprising, simultaneously with the recording, recording space and time varying signals representative of thermal emissions from the specimen during the activity.

7. The method of claim 1, wherein the recorded photon mages represent calcium ions.

8. The method of claim 1, wherein the recording and displaying are performed in real time.

9. The method of claim 1, further comprising filtering recorded data to visually display selected data.

10. The method of claim 1, further comprising storing the recorded images in a database.

11. The method of claim 10, further comprising comparing an image received in real-time to images stored in the database to determine if one or more of the previously stored images has a correlation with the currently received image.

12. The method of claim 1, wherein recording visual images is performed with a camera that captures a differential interference contract image.

13. The method of claim 1, further comprising making an audio recording of observations made of the images and recording the audio with the images so that the audio is heard while the images are played back.

14. The method of claim 1, wherein the method is performed to record a change in calcium ions during mitosis.

15. An apparatus for capturing images of a specimen during an activity of a specimen comprising:
   a first receiver that receives visual images of the specimen during the activity and provides a spatial and temporal visual recording of the specimen during the activity;
   a second receiver that receives space and time varying signals representing emissions of predetermined photons from the specimen during the activity simultaneously with the first receiver, the first and second receivers obtaining the images simultaneously; and
   a display that displays the spatial and temporal recording of the specimen and the signals representative of emissions of predetermined photons at the same time so that a user can visually see the activity and the photon emissions at the same time.

16. The apparatus of claim 15, wherein the display displays the visual images and the photon images in a superimposed manner.

17. The apparatus of claim 15, wherein the display isplays the visual images and the photon images adjacent one another.

18. The apparatus of claim 15, further comprising a microscope and a beam splitter for receiving images from the microscope, the beam splitter providing first and second signals to the respective first and second recorders.

19. The apparatus of claim 18, further comprising a processor that correlates the visual images and the photon emission signals.

20. The apparatus of claim 15, further comprising a third receiver that simultaneously receives and records space and time varying signals representative of emissions of a second predetermined photon from the specimen during the activity.

21. The apparatus of claim 15, further comprising a thermal detector receiving and recording space and time varying signals representative of thermal emissions from the specimen during the activity, the thermal detector receiving at the same time as the first and second recorders.

22. The apparatus of claim 15, wherein the photon signals are photons of calcium ions.

23. The apparatus of claim 15, further comprising means for visually coding the emission signals to represent their elapsed time from initial emission.

24. The apparatus of claim 15, further comprising means for filtering recorded data to visually display selected data.

25. The invention of claim 15, further comprising a storage device that stores previously received images, and a processor for comparing the stored previously received images with images received in real time.

26. The apparatus of claim 15, wherein the first receiver includes a video camera and a video cassette recorder.

27. The apparatus of claim 15, wherein the second receiver includes a photon counting camera.

28. The apparatus of claim 15, further comprising a stage for holding the specimen and a manipulator for manipulating the stage.

29. The apparatus of claim 15, wherein the first receiver takes a differential interference contrast image.

30. The apparatus of claim 15, further comprising an audio recording system for recording observational comments with the images so that the audio is heard while the images are played back.

31. The apparatus of claim 15, further comprising an image processor for receiving the images and for generating a representation that appears three-dimensional.

32. An apparatus comprising:

a microscope for imaging a cellular activity;

a beam splitter for dividing the image taken by the microscope between two outputs;

a video camera for receiving one output from the beam splitter;

a photon counting camera for receiving another output from the beam splitter;

a first video recorder for recording visual images received by the first video camera by which a user can see the activity;

a second video recorder for recording images from the photon counting camera; and an image processing system for forming a composite video recording of the outputs of the video camera and the photon counting camera superimposed on one another.

33. The apparatus of claim 32, further comprising a time code synchronizer that synchronizes the first and second video recorders with each other.

* * * * *

UNITED STATES PATENT AND TRADEMARK OFFICE
CERTIFICATE OF CORRECTION

PATENT NO : 6,078,681
DATED : June 20, 2000
INVENTOR(S) : Silver

It is certified that error appears in the above-identified patent and that said Letters Patent is hereby corrected as shown below:

In column 16, line 18, change "displaving" to, "displaying";

In column 16, line 36, change, "mages" to, "images";

In column 17, line 7, change, "isplays" to, "displays".

Signed and Sealed this

Eighth Day of May, 2001

*Attest:*

NICHOLAS P. GODICI

*Attesting Officer*   *Acting Director of the United States Patent and Trademark Office*